United States Patent [19]

Hammel

[11] Patent Number: 4,692,249
[45] Date of Patent: Sep. 8, 1987

[54] FLOTATION PROCESS FOR SLUDGE RECOVERY AND ENERGY CONVERSION

[76] Inventor: Gerard Hammel, 440 Senator St., Brooklyn, N.Y. 11220

[21] Appl. No.: 910,477

[22] Filed: Sep. 23, 1986

[51] Int. Cl.⁴ .......................... C02F 11/04; C02F 3/28
[52] U.S. Cl. .................................. 210/603; 210/170; 210/747; 210/242.1; 210/609; 435/167; 48/197 A
[58] Field of Search ...................... 210/170, 747, 242.1, 210/603, 601, 609; 435/167, 801; 48/197 A; 114/256, 257

[56] References Cited

U.S. PATENT DOCUMENTS 3,113,699  3/1963  Crawford et al.
3,435,793  1/1969  Shurtleff.
3,535,883  6/1970  Manning.
3,572,506  8/1971  Bandy, Jr.
3,590,887  4/1971  Quase.
3,833,122  3/1974  Cook.
4,046,178  4/1977  Case.
4,227,477  1/1980  Preus.
4,231,873  11/1980 Swigger.
4,579,654  4/1986  Bremmer ............................ 210/603
4,592,846  6/1986  Metzger et al. ..................... 210/747

FOREIGN PATENT DOCUMENTS 2500007   8/1982  France ................................. 435/167
2537158   6/1984  France ................................. 435/167
54-104641 8/1979  Japan .................................. 210/747
59-4713   1/1984  Japan .................................. 210/747
1089059   4/1984  U.S.S.R. ........................... 210/242.1

Primary Examiner—Benoit Castel
Attorney, Agent, or Firm—Brumbaugh, Graves, Donohue & Raymond

[57] ABSTRACT

Sewage is separated in an offshore facility into effluent and sludge. The effluent is used to provide nutrients to a seaweed farm. The sludge is transferred to flexible storage balloons and digested to produce methane which is recovered and dried. The digested sludge is then dried for fuel use.

3 Claims, 2 Drawing Figures

FLOTATION PROCESS FOR SLUDGE RECOVERY AND ENERGY CONVERSION

BACKGROUND OF THE INVENTION

This invention relates to the treatment of sewage, and particularly a process and apparatus for gasification and drying sewage sludge in an offshore facility.

Raw sewage is a very dilute liquid containing as much as 99.95% water. The low concentration of impurities makes purification of sewage costly. As a result, disposal of sewage without treatment has long been practiced. Increases in the volume of sewage, brought on by increased population and industrialization, have led to increased numbers of sewage treatment facilities, with a corresponding commitment of land and economic resources.

In a conventional sewage treatment facility, raw sewage is separated by screening, filtration, and sedimentation into a liquid effluent and sludge. The effluent contains water and dissolved materials, and is generally discharged from the sewage treatment facility. The sludge may then be subjected to anaerobic digestion by various species of microorganisms. This digestion tends to break down complex organics in the sludge and produce methane gas along with some hydrogen sulfide which may be burned for process heat or sold. The residual sludge may then be discharged, or in some cases it is dried and then used as fertilizer or burned.

Each of the procedures associated with conventional sewage treatment; especially sedimentation tanks, trickling filters, digester tanks and drying beds; requires substantial area. Further the building of a facility requires substantial capital investment at a very low rate of return.

SUMMARY OF THE INVENTION

It is an object of this invention to provide a process for the treatment of sewage sludge and the production of methane gas and a burnable solid or semi-solid fuel.

It is a further object of this invention to provide a process for the offshore treatment of sewage in which watery effluent is used as a nutrient in seaweed farms, and sludge is treated to produce methane gas and a burnable solid or semi-solid fuel.

In the process of this invention, sewage is separated into a watery effluent and sludge by sedimentation, filtration, or other known techniques at an existing sewage treatment facility or, preferably, at an offshore facility according to this invention. The offshore facility comprises a main foundation for the separation of sewage into effluent and sludge, and is surrounded by a seaweed farm. Effluent is discharged into the seaweed farm, supplying a nutrient rich environment. The seaweed may be harvested and used for example, as a feedstock in methane generation. The nutrient rich waters of the seaweed farm also serve as an excellent habitat for fish fry.

The separated sludge is pumped into large balloon digester tanks. These tanks are flexible, and readily movable when empty. Each tank is constructed so that, when used in an offshore facility, it has sufficient buoyancy to float, even when filled with effluent. In offshore use, the balloon storage tank may be towed away from the main foundation and anchored for storage during methane generation.

Sludge sealed in an anaerobic environment will be digested by indigenous bacteria producing methane. This methane can be recovered through fittings in the top of the balloon storage tank, either continuously, or at intervals during the digestion.

When methane production has slowed down, the sludge remaining in the balloon storage tanks is removed and placed in drying beds. These drying beds are shallow containers, which may optionally be lined with a disposable liner and, in the case of an offshore facility, may be located on barges.

Covering each drying bed is a transparent cover. These covers permit accumulation of solar heat to accelerate drying, but should be well vented to allow air circulation and escape of moisture. The covers are also designed such that, in case of rain, or rough seas, water does not reach the sludge to any significant extent.

After drying is complete, the sludge cake is removed from the drying tank. The dried sludge may be used as a fertilizer or burned as a fuel.

DETAILED DESCRIPTION OF THE INVENTION

Figure 1:
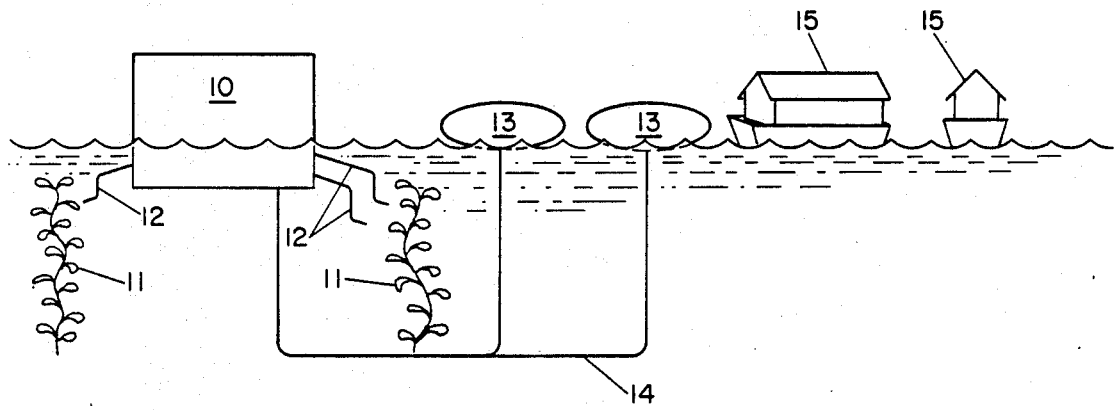
FIG. 1 shows a schematic of a complete sewage treatment facility according to the invention.

In a preferred embodiment of this invention, sewage is treated in an offshore facility using balloon storage tanks and covered drying beds located on barges. As shown in FIG. 1, raw sewage is piped under water to a main foundation 10 located offshore. This main foundation contains sedimentation tanks and other equipment to separate sewage into effluent and sludge.

Surrounding the main foundation, except for channels for barge traffic, is a seaweed farm 11. Effluent separated from the sewage is distributed throughout the seaweed farm through a network of tubes 12 providing a nutrient-rich environment. The seaweed farm serves as an excellent habitat for fish fry, thus promoting local fisheries. The seaweed is periodically harvested and may be processed as a source of protein. Alternatively, the harvested seaweed may be used as a feedstock for microorganisms, particularly methanogens.

Sludge from the main foundation is pumped into balloon storage tanks 13. The balloon storage tanks are towed to a nearby area, and digestion allowed to proceed. Undersea connections 14 may optionally be supplied to the digestion area to carry methane back to the main foundation. In this case, the low temperature at the bottom of the connecting tube can be used to condense water vapor, purifying the methane gas. Periodic pressurization of the line can be used to purge the condensed water from the line.

After methane production has proceeded for the desired time, the balloon storage tank is moved to the drying area and the sludge is transferred to a covered drying barge 15. Sludge may be removed from the balloon storage tank by pumping or vacuuming. Using a preferred storage tank, water is pumped into the space between the inner liner and the outer layers, forcing the sludge out of the balloon storage tank and into the barge. The water-filled balloon storage tank is then returned to the main foundation 10, and the water is then displaced by refilling the balloon storage tank with fresh sludge.

After the sludge in the covered drying barge 15 is dried, the barge is moved to the main foundation 10 or to an unloading point on shore. One or more sides and the cover of the barge are preferably removable to facilitate removal of the dried sludge cake. The dried sludge may then be burned as a fuel, or supplemented and used as a fertilizer.

Figure 2:
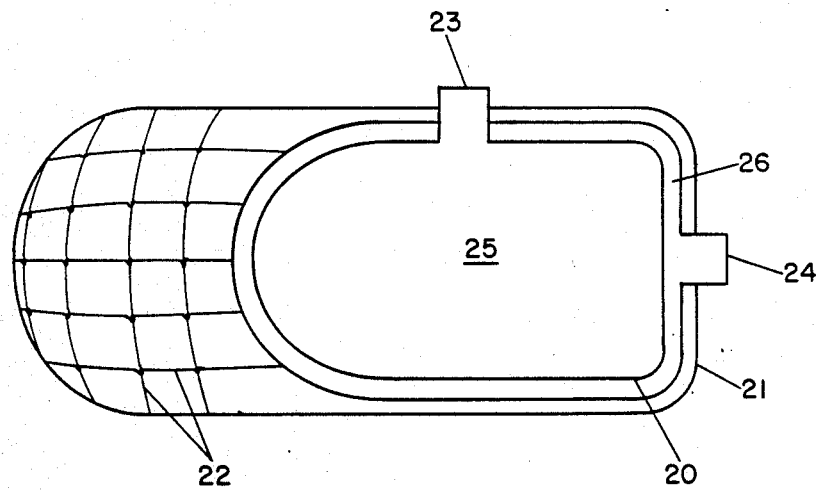
FIG. 2 shows, in partial section, a balloon storage tank.

Following the separation of sewage into effluent and sludge, the sludge is pumped into balloon storage tanks for digestion. Looking to FIG. 2, a three-layered construction for a preferred balloon storage tank according to the invention is shown. The inner layer 20 is a lightweight and very flexible material which is resistant to degradation by the sludge. Optionally, this layer may be disposable, being replaced periodically with a new inner liner.

Exterior to the inner liner 20 is a second layer 21. This layer is not joined to the inner liner 20 except where fittings, such as fitting 23, pass through the wall of the balloon storage tank to provide access to the inner storage space 25. The second layer 21 is made of a fluid impermeable, corrosion and weather resistant material. This layer is preferably seamed to minimize the risks of an explosive blowout due to methane gas pressure. Outside of layer 21 is a covering of rope mesh or netting 22. This netting further stabilizes the seamed outer layer to minimize the risk of a large explosion, and may optionally serve as a means for attaching an anchor line to the balloon storage tanks in offshore use. Additional layers may be added, as desired, to improve strength, or to impart added buoyancy to the balloon storage tanks.

A fitting 23 located on the top of the balloon storage tank is used to connect hoses for pumping sludge in and out of the balloon storage tanks, and for the removal of methane gas produced by sludge digestion. Fitting 23 passes through all layers of the balloon storage tank, and connects to the interior cavity 25 of the inner liner 20.

Optionally, a second fitting 24 may be located on the side of the balloon storage tank. Fitting 24 does not pass through the inner liner 20, but instead connects to the space 26 between the inner liner 20 and the second layer 21. Air or water may be pumped through fitting 24 to adjust the buoyancy of the balloon storage tank. Optionally, water may be pumped into space 26 causing sludge present in the inner cavity 25 to be forced out through fitting 23. For land use, the balloon storage tank may optionally be equipped with two or more fittings on the side to allow the passage of cooling water through space 26.

Drying beds may be used to dry sludge removed from the balloon storage tanks. These drying beds are essentially shallow tanks and may contain layers of sand and gravel to carry away moisture from the bottom. Optionally, a disposable liner may be used in the drying beds.

The drying beds are covered with a preferably transparent cover which serves to retain heat and prevent rain or spray from entering the bed, while at the same time permitting escape of moisture. To accomplish these goals, the cover is preferably well vented to provide for air circulation but in such a manner that water is unlikely to enter through the vents. For example, a soffit and ridge vent combination with interior baffles to prevent entry of water could be used.

I claim:

1. A process for offshore sewage treatment comprising:
   (a) separating sewage into a watery effluent and a sludge;
   (b) placing the sludge in flexible buoyant balloon storage tanks for anaerobic digestion;
   (c) recovering and drying methane produced from the sludge during said digestion;
   (d) transferring the sludge to drying barges;
   (e) drying the sludge; and
   (f) supplying the watery effluent to surrounding seaweed farms as a nutrient.

2. The process of claim 1, wherein the methane is dried by piping it to a depth where the temperature is sufficiently low so that water vapor condenses.

3. The process of claim 1, wherein the sludge is transferred to a drying barge by pumping water into the space between layers of the balloon storage tanks and displacing the sludge.

* * * * *